United States Patent
Berry et al.

(10) Patent No.: US 9,323,893 B2
(45) Date of Patent: Apr. 26, 2016

(54) USING MOBILE CONSUMER DEVICES TO COMMUNICATE WITH CONSUMER MEDICAL DEVICES

(75) Inventors: Matthew M Berry, Highland, UT (US); Robert M. Berry, Highland, UT (US); Wesley D. Chapman, Draper, UT (US); Jacob S. Lybbert, Provo, UT (US)

(73) Assignee: ORCA HEALTH, INC., Sandy, UT (US)

( * ) Notice: Subject to any disclaimer, the term of this patent is extended or adjusted under 35 U.S.C. 154(b) by 1331 days.

(21) Appl. No.: 13/167,600

(22) Filed: Jun. 23, 2011

(65) Prior Publication Data
US 2013/0142367 A1 Jun. 6, 2013

(51) Int. Cl.
*H04R 25/00* (2006.01)
*G06F 19/00* (2011.01)

(52) U.S. Cl.
CPC .......... *G06F 19/327* (2013.01); *G06F 19/3412* (2013.01); *G06F 19/3418* (2013.01)

(58) Field of Classification Search
CPC .. H04R 25/70; H04R 2225/55; H04R 25/554; H04R 1/1091; H04R 2225/41; H04R 25/43; H04R 25/55; H04R 25/552; H04R 25/558; H04R 11/02; H04R 1/1016; H04R 1/406; H04R 2205/041; H04R 2225/33; H04R 2225/61; H04R 2227/003; H04R 25/602; H04R 27/00; H04R 5/04; G06F 19/3418; G06F 19/3406; G06F 19/3412; G06F 19/3456; G06F 19/322; G06F 19/3468; G06F 19/3487; G06F 8/65; G06F 19/327; G06F 19/345; G06F 19/3475; A61N 1/37211; A61N 1/37264; A61N 1/37282; A61M 2005/14208; A61M 2005/14296; A61M 2205/17; A61M 2205/3303; A61M 2205/3569; A61M 2205/50; A61M 2205/52; A61M 2205/702; A61M 2230/201; A61M 5/14; H04L 27/2602; H04L 27/2627; H04L 67/02; H04L 67/125; H04L 67/34; H04L 69/08; H04L 7/10; H04W 12/06; H04W 24/02; H04W 4/001; H04W 4/008; H04W 4/025; H04W 4/12; H04W 4/16; H04W 4/22
USPC ...................... 381/312, 314, 315, 60; 702/19; 600/300, 301; 607/30; 455/569.1
See application file for complete search history.

(56) References Cited

U.S. PATENT DOCUMENTS 6,804,558 B2 * 10/2004 Haller et al. .................... 607/30
7,181,505 B2 * 2/2007 Haller et al. .................. 709/219
(Continued)

OTHER PUBLICATIONS

Iltifat Husain, MD "Apple finally joins Bluetooth standards group, could usher in new era of bluetooth medical devices", Available http://www.imedicalapps.com/2011/06/apple-bluetooth-standards-medical-peripheral-devices/ . printed Jun. 21, 2011. 1 pg.

(Continued)

*Primary Examiner* — Davetta W Goins
*Assistant Examiner* — Phylesha Dabney
(74) *Attorney, Agent, or Firm* — Workman Nydegger

(57) ABSTRACT

Mobile consumer devices are used to communicate with consumer medical devices to either provide update data to the consumer medical device or to obtain data from the consumer medical device. Some data is used to evaluate performance and operation of the medical device or a biological condition of the living being that is being treated with the medical device. Other data is used to calibrate and update the consumer medical device or to enable or disable certain functionality of the medical device. Communications between the medical devices and mobile consumer devices can be performed automatically or on demand, as initiated by a user, a third party, or in response to predetermined conditions detected by the devices.

16 Claims, 2 Drawing Sheets

(56) References Cited

U.S. PATENT DOCUMENTS

| | | | |
|---|---|---|---|
| 8,068,630 B2* | 11/2011 | Gable et al. | 381/322 |
| 8,494,196 B2* | 7/2013 | Zukic | 381/314 |
| 2011/0299709 A1* | 12/2011 | Anderson et al. | 381/315 |
| 2011/0320130 A1* | 12/2011 | Valdes et al. | 702/19 |
| 2012/0050685 A1 | 3/2012 | Bartlett et al. | |
| 2013/0141697 A1 | 6/2013 | Berry et al. | |
| 2013/0308802 A1* | 11/2013 | Eaton et al. | 381/314 |
| 2013/0315424 A1* | 11/2013 | Eaton et al. | 381/314 |
| 2014/0168606 A1 | 6/2014 | Berry et al. | |

OTHER PUBLICATIONS

U.S. Appl. No. 14/482,844, filed Sep. 10, 2014, Berry et al.
U.S. Appl. No. 14/251,400, filed Apr. 11, 2014, Mainwaring et al.
U.S. Appl. No. 62/045,968, filed Sep. 4, 2014, Mainwaring et al.
Newman, Lily Hay, "Control This Hearing Aid With Your iPhone", Future Tense: The Citizen's Guide to the Future, Feb. 25, 2014, Available at <<http://www.slate.com/blogs/future_tense_2014/02/25/resound_linux_hearing_aid_works_with_the_iphone.html>>.
Leber, Jessica, "The End of Eye Charts? A Startup Can Now Give Eyeglass Exams Online", Co.EXIST, Published Mar. 20, 2014, Available at <<http://www.fastcoexist.com/3027090/the-end-of-eye-charts-a-startup-can-now-give-eyeglass-exams-online>>.
U.S. Appl. No. 13/167,610, filed Jun. 17, 2013, Office Action.
U.S. Appl. No. 13/167,610, filed Dec. 9, 2013, Notice of Allowance.
U.S. Appl. No. 14/189,180, filed Mar. 28, 2014, Office Action.
U.S. Appl. No. 14/189,180, filed Jul. 16, 2014, Notice of Allowance.
U.S. Appl. No. 13/167,600, filed Aug. 25, 2014, Office Action.
U.S. Appl. No. 14/482,844, Feb. 2, 2016, Notice of Allowance.

* cited by examiner

USING MOBILE CONSUMER DEVICES TO COMMUNICATE WITH CONSUMER MEDICAL DEVICES

CROSS-REFERENCE TO RELATED APPLICATIONS

Not applicable.

BACKGROUND

1. The Field of the Invention

This invention relates to systems, methods, and computer program products that facilitate communications between mobile consumer devices and consumer medical devices and/or other third party systems. Some of the communications are operable to update the consumer medical devices, to initiate functionality at the medical devices and/or to gather data from the consumer medical devices.

2. The Relevant Technology

Modern technology has produced many consumer medical devices that can enhance and extend human life. This technology has advanced from simple consumer medical devices such as ear horns and wooden peg legs to far more complex devices such as cochlear implants and robotic prosthetic limbs. Such devices can significantly improve the quality of a user's life and, in some instances, increase the user's ability to contribute to society and enjoy a rewarding life.

Many of the advances within the medical industry have resulted from the application of electronic technologies. Unfortunately, these advances are often offset by the cost and inconveniences associated with having to monitor, calibrate, and update the electronics that are embedded within the medical devices.

Oftentimes, the user will be unaware of the need to calibrate or update the device which may lead to a broad range of medical consequences. For example, a hearing aid needing calibration can result in annoying feedback or a loss of hearing. A pacemaker needing calibration can result in far more serious consequences, such as heart attack or death.

Sometimes a user will be suspicious as to the operable condition of a medical device, so they will schedule an appointment with a specialist to test the device. Whether the medical device is working properly or not, the test will often represent wasted resources. In particular, the user's time spent during the test could have been applied to other activities, such as productive work, and the doctor's time could have been spent treating someone with a real medical condition (which could also be more profitable). If the test confirms that the user's device is malfunctioning, the benefit of the test can sometimes outweigh the costs and inconveniences. But, if the device is functioning properly, the test will result in little to no benefit. In some instances, the costs and inconveniences of performing a test can deter a user from testing a device when it should be tested.

In recent years users have made attempts to analyze consumer medical devices using information from the Internet. For instance, a user can type the name and/or model number of the device into a search engine and a vast array of information is presented to the user for the user's consumption. This information may include user manuals, schematics, answers to commonly asked questions and other related information. No existing systems are provided, however, for testing and analyzing a user's individual medical device, such as a hearing aid, through the Internet.

Accordingly, there remains some room for further development in the field of communication with consumer medical devices.

BRIEF SUMMARY

The present invention extends to methods, systems, and computer program products for facilitating communication between consumer medical devices and other computing devices, including mobile consumer devices.

One embodiment includes a method in which a wireless communication is initiated between a mobile consumer device and a medical device attached to a user. The communication is used to obtain metric data from the medical device (about the device or the user), to update the medical device, and/or to initiate functionality at the medical device.

The communications between the mobile consumer device and the consumer medical device can be manually initiated by the user or a third party or can be automatically initiated according to a predefined periodic interval.

In some embodiments, the user's mobile consumer device prompts the user to identify one or more consumer medical devices to communicate with and receives user input selecting the one or more consumer medical devices. Based on the selection by the user, the mobile consumer device establishes a communication channel. Authentication requiring tokens or passwords can also be required from the user and/or mobile consumer device prior to establishing the communication channel.

Another embodiment can involve a medical professional or other third party remotely initiating the communication channel between the mobile consumer device and the consumer medical device. This communication channel can also be extended to include a three way communication between the third party, the mobile consumer device and the consumer medical device, with the mobile consumer device operating as an intermediary between the third party system and the consumer medical device. In such embodiments, the medical professional can be presented with a prompt to select the one or more consumer medical devices with which to establish a communication channel. Based on the input from the medical professional, the mobile consumer device establishes a communication channel with the one or more medical devices and interconnects the third party system to the consumer medical device(s).

In another embodiment, the consumer medical device and/or the mobile consumer device initiates the establishment of the communication channel based on detecting one or more conditions at the consumer medical device and/or the mobile consumer device.

Once the communication channel is established, embodiments of the invention include updating the medical device(s) and obtaining metric data from the medical device(s).

This Summary is not intended to identify key features or essential features of the claimed subject matter, nor is it intended to be used as an aid in determining the scope of the claimed subject matter.

Additional features and advantages of exemplary implementations of the invention will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims, or may be learned by the practice of such exemplary implementations as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

Figure 1:
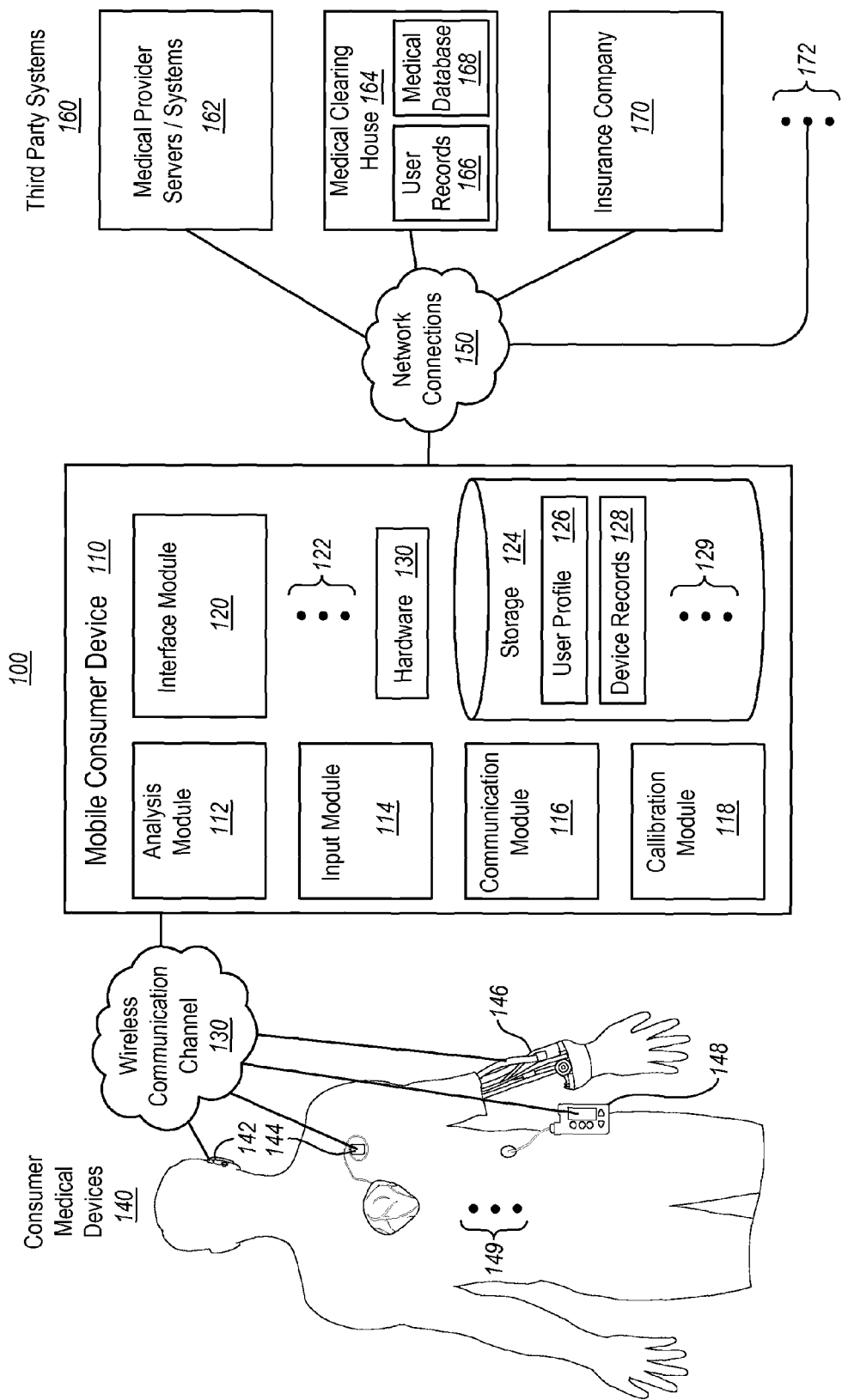
FIG. 1 illustrates a computing environment that can be used to facilitate communications between a mobile consumer device and one or more consumer medical devices, as well as third party systems via network connections.

The present invention extends to methods, systems, and computer program products for facilitating communication between mobile consumer devices and consumer medical devices.

Some embodiments include acts associated with establishing and using a wireless communication channel between a mobile consumer device and the consumer medical device to update the consumer medical device, identify metric data that is accessible through the consumer medical device, initiate emergency procedures, or recommend user actions.

Some embodiments include using mobile consumer devices such as wireless phones, tablets, and smart devices to communicate with consumer medical devices, such as hearing aids, prosthetics, insulin pumps, pacemakers, and other consumer medical devices attached to a living being.

Computing Environment(s)

Embodiments of the present invention may comprise or utilize special purpose or general-purpose computing devices that include computer hardware, such as, for example, one or more processors and system memory, as discussed in greater detail below. Embodiments within the scope of the present invention also include physical and other computer-readable and recordable type media for carrying or storing computer-executable instructions and/or data structures. Such computer-readable recordable media can be any available media that can be accessed by a general purpose or special purpose computer system. Computer-readable media that store computer-executable instructions according to the invention are recordable-type storage media or other physical computer storage media (devices) that are distinguished from mere transitory carrier waves.

Computer-readable media that carry computer-executable instructions are transmission media. Thus, by way of example, and not limitation, embodiments of the invention can comprise at least two distinctly different kinds of computer-readable recordable media: computer storage media (devices) and transmission media.

Computer storage media (devices) includes RAM, ROM, EEPROM, CD-ROM or other optical disk storage, magnetic disk storage or other magnetic storage devices, or any other medium which can be used to store desired program code means in the form of computer-executable instructions or data structures and which can be accessed by a general purpose or special purpose computer and which are recorded on one or more recordable type medium (device).

A "network" is defined as one or more data links or communication channels that enable the transport of electronic data between computer systems and/or modules and/or other electronic devices. When information is transferred or provided over a network or another communications connection or channel (either hardwired, wireless, or a combination of hardwired or wireless) to a computer, the computer properly views the connection as a transmission medium. Transmissions media can include a network and/or data links which can be used to carry or desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to computer storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. Thus, it should be understood that computer storage media (devices) can be included in computer system components that also (or even primarily) utilize transmission media.

Computer-executable instructions comprise, for example, instructions and data which, when executed at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described herein. Rather, the described features and acts are disclosed as example forms of implementing the claims.

Those skilled in the art will appreciate that the invention may be practiced in network computing environments with many types of computer system configurations, including, personal computers, desktop computers, laptop/notebook computers, message processors, hand-held devices, multi-processor systems, microprocessor-based or programmable consumer electronics, network PCs, minicomputers, mainframe computers, tablets, mobile telephones, PDAs, pagers, routers, switches, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

In particular, one or more embodiments of the invention may be practiced with mobile consumer computing devices. Mobile consumer computing devices or more simply, mobile consumer devices, can be any of a broad range of computing devices designed or optimized for portability and for personal use. Mobile consumer devices can take a variety of forms, ranging from more traditional notebook and netbook computers to an emerging and rapidly growing market of handheld devices, including smart phones (e.g., the APPLE IPHONE, ANDROID phones, WINDOWS phones, SYMBIAN phones), tablet computers (e.g., the APPLE IPAD, ANDROID tablets), gaming devices (e.g., NINTENDO or PLAYSTATION portable gaming devices, the APPLE IPOD), multimedia devices (e.g., the APPLE IPOD), and combinations thereof. Many of these devices can enable rich user-interactivity by including combinations of output, input, and other sensory devices, such as touch- or pressure-sensitive displays (using capacitive or resistive technologies, for example), still and video cameras, Global Positioning System (GPS) receivers, magnetic compasses, gyroscopes, accelerometers, light sensors, proximity sensors, microphones, speakers, etc. These devices can also comprise a variety of communications devices, such as combinations of cellular modems (e.g., Global System for Mobile Communications (GSM), Code division multiple access (CDMA)), Wireless Fidelity (Wi-Fi) radios, Bluetooth radios, Near Field Communication (NFC) devices, etc. Many mobile consumer devices are expandable, such that a user can add new hardware and functionality not present during manufacture of the device. It will be appreciated that as the market for mobile consumer devices expands and develops, the functionality of these devices will also expand to utilize new and improved user-interaction devices and communications devices. The embodiments described herein are expansive and can also utilize any future developments in the field of mobile consumer devices.

Communications with Consumer Medical Devices

Embodiments of the invention can be utilized to facilitate communications between consumer medical devices and computing devices, including mobile consumer devices and third party computing systems.

The disclosed communication methods can further enable users and medical professionals to update and configure consumer medical devices, identify metric data from the medical devices, and initiate emergency actions and other functionality at the medical devices.

The ability to communicate with consumer medical devices in accordance with aspects of the invention can also mitigate many of the costs and inconveniences associated with a user traveling to a medical facility to have a medical professional perform an evaluation of or update/configure their medical device(s). Much of the time wasted, searching on the Internet for answers to common problems, in an attempt to manually troubleshoot a malfunctioning device, can also be avoided because of the ease and convenience of using a mobile consumer device which the user is familiar with. A user can also be more informed about the state of their medical device by being able to download data from the medical device to their mobile device. This can also significantly decrease the probability that the operable state of the medical device will be misdiagnosed by the user and, in some instances, the medical professional.

FIG. 1 illustrates an exemplary computing environment 100 that can be used to facilitate communications between consumer medical devices and other computing devices, such as mobile consumer devices and third party systems.

As shown, the computing environment 100 includes a mobile consumer device 110 in communication with one or more consumer medical devices 140 through a wireless communication channel 130. The wireless communication channel 130 can be established via Bluetooth, infrared, Wi-Fi, cellular, or any other kind of digital or analog radio wave channel. In some embodiments, these devices can also be connected via a hardwire connection.

The mobile consumer device 110 is also shown to be in communication with one or more third party systems 160 through one or more network connections 150. These network connections can include any combination of Local Area Network ("LAN") connections, Wide Area Network ("WAN") connections, including the Internet.

Each of the depicted systems and devices are capable of creating message related data and exchanging message related data (e.g., Internet Protocol ("IP") datagrams and other higher layer protocols that utilize IP datagrams, such as, Transmission Control Protocol ("TCP"), Hypertext Transfer Protocol ("HTTP"), Simple Mail Transfer Protocol ("SMTP"), etc.) over the various network connections 150 and wireless communication channels 130.

It will be appreciated that the computing environment 100 can include any number of consumer medical devices. The illustrated computing environment 100 presently identifies four specific consumer medical devices 142, 144, 146, and 148. However, the ellipses 149 illustrate that any number of additional consumer medical devices can also be utilized according the inventive concepts described herein. Similarly, it will be appreciated that the invention does not necessarily require a plurality of medical devices to be utilized by a single user at any given time, inasmuch as it is clearly possible for the computing environment 100 to only utilize a single consumer medical device for a particular user.

It will also be appreciated that each of the illustrated systems and devices can also comprise a standalone system (as generally shown) or, alternatively, distributed systems and devices.

As illustrated, the mobile consumer device 110 is configured with a plurality of components that facilitate communication with one or more consumer medical devices 140. Mobile consumer device 110, for example, can include an analysis module 112, an input module 114, a communication module 116, a calibration module 118, an interface module 120, and a storage component 124. As indicated by the ellipses 122, the mobile consumer device can also include any number of additional components, and can include many different arrangements of components while still falling within the scope of this disclosure.

The analysis module 112 includes computer-executable instructions that, when executed by a processor of the mobile consumer device, are operable to facilitate analysis of data received from the consumer medical devices, third party systems and a user or medical professional and to determine whether predetermined conditions have been satisfied to initiate a communication or procedure with the consumer medical device 140.

The input module 114 includes computer-executable instructions that, when executed by a processor of the mobile consumer device, are operable to facilitate the receipt of input entered at the mobile consumer device 110 or that is transmitted to the mobile consumer device through the wireless communication channel 130 or the network connections 150.

The communication module 116 includes computer-executable instructions that, when executed by a processor of the mobile consumer device, are operable to facilitate wireless communications over the wireless communication channel or the network connections 150.

The calibration module 118 includes computer-executable instructions that, when executed by a processor of the mobile consumer device, are operable to facilitate the generation of and/or transmission of calibration instructions to the consumer medical device 140.

The interface module 120 includes computer-executable instructions that, when executed by a processor of the mobile consumer device, are operable to generate and/or present user interfaces to a user for presenting data, receiving data and/or communicating with the mobile consumer device 110.

The storage component 124 is configured to store a variety of data (i.e., metadata), metric data, image data, interfaces, third party contact data, user profile data, device profile data, and the various modules of the mobile consumer device 110. The data retained by and/or accessed by storage component 124 facilitates communication with the consumer medical devices 140, including information from user profile 126 and device records 128. The data can include metric data that is stored over time from one or more consumer medical devices, and metric data from the user including applicable medical history information, such as past treatment information, past communication results, information about treating physicians and/or treatment facilities used by the user, prescription information, and the like. The user profile 126 data and device records 128 data can also include state information corresponding to a detected state of operation of the medical devices or condition of a biological system associated with the user.

As indicated by ellipses 129, the storage on the mobile consumer device can store any type and quantity of different data, being limited by only the size of the storage 124. It will be appreciated; however, that storage 124 can be distributed among a plurality of different devices, including the third party systems, and does not necessarily need to be constrained in a single physical device. In some embodiments, however, the storage 124 is constrained to a single mobile consumer device.

In some embodiments, the mobile consumer device 110 comprises a wireless cell phone, a tablet computer, a netbook computer, a PDA, and/or any other type of smart device having a display screen and/or speakers that are included within the hardware 130 of the mobile consumer device and that are capable of rendering image data and/or audio data to a user via the interface module 120, for example. In some embodiments, the hardware 130 of the mobile consumer device 110 also includes a touch screen capable of receiving touch input at the display screen.

It will be appreciated that display and audio hardware (130) of the mobile consumer device can be particularly useful during implementation of various embodiments described herein to enable the medical professional(s) and user(s) to remotely interface via video conferencing or teleconferencing during the various medical procedures that are described herein.

Each of the mobile consumer device 110, consumer medical devices 140 and the third party systems 160 include hardware, storage, and software components necessary to implement the functionality of the invention, and can include, therefore, any of the hardware and software components described throughout this paper. For instance, it will be appreciated that the consumer medical devices (140) also include various hardware, processors, and storage having stored instructions and modules, similar to or the same as the modules of the mobile consumer device, for facilitating wireless communications as well as the other functionality described herein.

In some embodiments, the consumer medical devices include Bluetooth or other wireless components that are connected to hardware processors and storage components. The medical devices 140 also include digital and/or mechanical mechanisms that are operable to facilitate the functionality of the consumer medical devices and can, in some instance, include sensors, probes, batteries or other power supplies, drug delivery devices, and corresponding drugs.

As shown in FIG. 1, the one or more consumer medical devices 140 are connected directly to a living being. It will be appreciated, however, that the living being can be an animal other than a human and, in some instances, even a plant. Furthermore, it is not necessary that the living being be the actual owner or user of the mobile consumer device.

Some examples of applicable consumer medical devices are a hearing aid 142, a pacemaker 144, a prosthetic limb 146, and an insulin pump 148. However, as indicated by the ellipses 149, there can be any number of other consumer medical devices with which a mobile consumer device can connect, including, but not limited to organ dialysis machines, animal control devices (e.g., bark collars), plant analysis machines, and so forth.

Third party systems can include any combination of medical provider servers and systems 162, medical clearing houses 164, insurance companies 170, or other third parties 172 with which the mobile consumer device can connect via network connections 150. In some embodiments, the additional third parties 172 include other mobile consumer devices, such as mobile consumer devices of a caretaker or family member of the user having the attached consumer medical device(s) 140.

The network connections 150 to medical provider servers/systems 162 allow the mobile consumer device 110 to access patient data, to recommend settings for the consumer medical device(s) 140, and to access other data from a user's medical professional that is specific to the user. Among other things, this data can be used by the mobile consumer device 110 when accessing metric data from the one or more consumer medical devices 140 for analysis. When desired, the metrics of the one or more consumer medical devices 140 can also be reviewed by medical professionals.

In some embodiments, the establishment of the wireless communication channel 130 and communications between the mobile consumer device 110 and the consumer medical device(s) 140 is initiated by the user of the mobile consumer device 110. The user can also initiate communications between the mobile consumer device 110 and the third party systems 160. This embodiment can be particularly beneficial for enabling a user to obtain information about their consumer medical device(s) 140 and to initiate functionality changes or recalibration of their consumer medical device(s) 140, without having to make an in person trip to an office space of a medical professional.

In other embodiments, the establishment of the wireless communication channel 130 and communications between the mobile consumer device 110 and the consumer medical device(s) 140 is initiated by medical professionals or other third parties. The third parties can also initiate the communications between the mobile consumer device 110 and the third party systems 160. This embodiment can be particularly useful for enabling a medical professional to initiate and/or conduct a check-up on a patient or a patient's consumer medical device without requiring the patient to first schedule an in-person visit.

In some embodiments, the medical professional can initiate a modification of the functionality of the consumer medical device 140, such as a calibration of the medical device, turning off certain functionality of the medical device, turning on subscribed for functionality or features of the medical device, providing updates to the medical device or receiving metric data from the medical device.

Another application of the foregoing is a remotely initiated emergency diagnosis and procedure. For instance, a medical professional can be immediately notified of irregular activity of one or more consumer medical devices 140. For instance, if a pacemaker 144 malfunctions, rather than leaving a user to save himself or requiring a user to reach a hospital prior to receiving treatment, a medical professional can be remotely notified of the condition in response to communications that are transmitted through the various devices and systems described above. The medical professional can then assess the information and take appropriate action. In one embodiment, the medical professional can remotely communicate with the consumer medical device 140 to provide an update or initiate a modification or procedure with the one or more consumer medical device 140. In the case of a malfunctioning pacemaker or a detected heart attack, the medical professional can remotely initiate a defibrillation process or modification of the pacemaker functionality, thus potentially saving a life. In other embodiments, a medical professional can remotely initiate the injection of a drug from a corresponding medical device. Various other procedures can also be initiated.

It will be appreciated that the medical professional can remotely initiate the foregoing procedures using a three way communication between the third party system 160, the mobile consumer device 110 and the consumer medical devices 140 using the wireless communication) channel 130 and the network connections 150. In other embodiments, the third party systems 160 can bypass the mobile consumer device 110 and communicate directly with the consumer medical devices 140 via a wireless communication link, or another network connection (not shown).

It will be appreciated that while various procedures described above can be initiated directly in response to manual input entered by a user or a medical professional at one of the devices or systems described herein, the procedures do not all require manual intervention. In fact, according to some embodiments, the communications and procedures described herein are initiated automatically at any one of the consumer medical devices 140, the mobile consumer devices 110, or third party systems in response to predetermined conditions detected by the devices and/or systems.

Turning briefly to the medical clearing house 164, the storage in the clearing house contains user records 166 and a medical database 168. This information can include all or some of the information stored in the storage component(s) 124 of one or more mobile consumer devices 110. As such, user records 166 can store consumer medical device history, medical history of the user, configuration information, and the like. Whereas storage component 124 would typically store general information for users of the corresponding consumer medical device, the storage components 166 and 168 at the clearing house 164 may store information applicable to users of a plurality of consumer medical devices (e.g., information for any combination of consumer medical devices 142, 144, 146, 148, or any other consumer medical device). The medical clearing house 164 can thus store all or part of information that is usable by a plurality of users of consumer medical devices 140. The medical clearing house 164 can also store preference data for different medical professionals and insurance information related to services and products that are utilized by or referenced during any of the communications with the consumer medical devices 140 described herein.

Insurance company 170 can also receive information routed from the mobile consumer device 110 through the network connections 150 to verify and substantiate claim processing and/or to automatically initiate the claims processing in response to detecting the various medical procedures utilizing the time and services of the medical professionals, software and devices.

Figure 2:
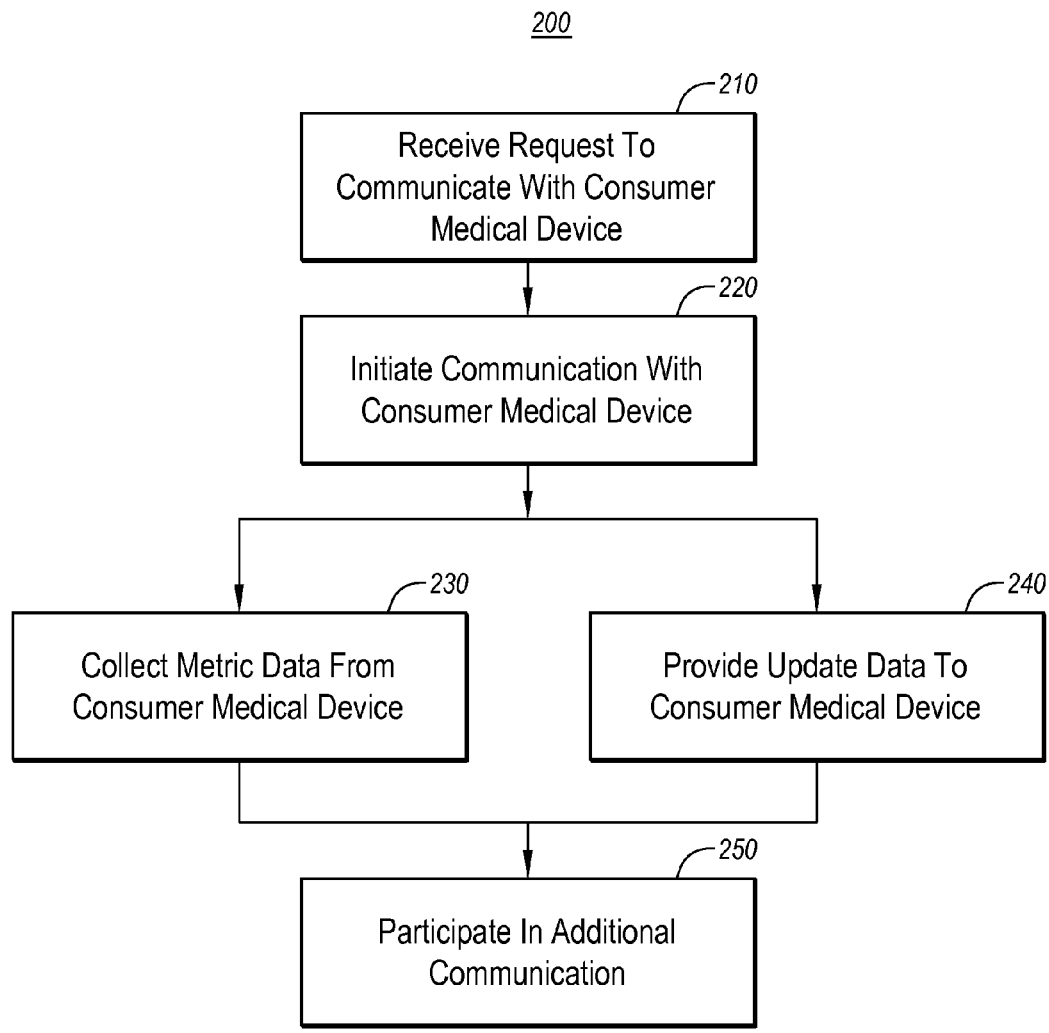
FIG. 2 illustrates a flow chart of acts associated with methods of the invention for collecting metric data from medical devices and for providing updates to the medical devices via mobile consumer devices.

Attention will now be directed to FIG. 2, which illustrates a flow diagram 200 of various acts associated with disclosed methods of the invention. For instance, the flow diagram 200 includes the acts of receiving a request to communicate with a consumer medical device (210), an act of initiating communication with a consumer medical device (220), as well as acts of collecting metric data from the medical device (230) and providing update data to the consumer medical device (240). The methods of the invention can also include various other acts, including an act of participating in additional communication (250). This additional communication can include video conferencing, follow-up communications and other communications that are not explicitly included as part of the metric downloading or updating described in acts 230 and 240.

The various acts of the flow diagram 200 will now be described in greater detail, with specific reference to some of the components of FIG. 1. Notably, the various acts are recited from the perspective of the mobile consumer device. However, correspondingly appropriate acts are also performed by the consumer medical devices and third party systems.

The first act (210), of receiving a request to communicate with a consumer medical device, corresponds directly to the process of establishing communication between a mobile consumer device and a consumer medical device via a wireless communication channel. This request can be received from the user of the mobile consumer device 110 using the input module 114 and interface module 120 of the mobile consumer device 140 and any corresponding interfaces that are presented at the mobile consumer device 110. For instance, a user can interact with an application at the mobile consumer device which prompts the user to identify one or more consumer medical devices with which to establish communication.

In another embodiment, the mobile consumer device receives a request to communicate with a consumer medical device (210) from the consumer medical device 140. This might occur automatically, according to a predefined periodic schedule, or in response to the consumer medical device 140 detecting a predefined condition of the user or the device 140, such as a device malfunction or a low battery/power condition. In some instances, the user of a consumer medical device 140 may not notice that the device is malfunctioning until he or she has suffered negative consequences as a result of the malfunction. For instance, the user of an insulin pump might not notice that the device is malfunctioning until they experience dizziness or fainting. Similarly, a user of a hearing aid may not know that the hearing aid needs calibration because they have not experienced a complete loss of hearing for most sounds rendered at certain volumes or frequencies. Accordingly, rather than waiting until the malfunction is fully or even partially manifest to the user, the consumer medical device 140 can detect a predefined condition and initiate communication with the mobile consumer device 110.

In some instances, the mobile consumer device 110 initiates communication to provide updates to the consumer medical device. In other instances, the consumer medical device 140 initiates the request to communicate with the mobile consumer device 110 to request/receive the software updates.

In some embodiments, requests can be automatically granted with or without user input. In other embodiments, requests can be routed to a medical professional for review and/or for authorization prior to enabling requested communications. In this regard, the medical professional can operate as a gatekeeper to any modifications and procedures performed with the medical device. This embodiment can be useful for allowing the medical professional or another third party to regulate which of a plurality of features are enabled at the consumer medical device. This can be particularly useful when the available features/functionality of the consumer medical device must be selectively subscribed for and paid for.

In some instances, the medical professional can receive automatic alerts if one or more consumer medical devices 140 report metric data corresponding to a malfunction of the medical device or a condition of a user that needs attention. For example, if a hearing aid malfunctions or needs calibration, the device can send a request to initiate communications that will include update data, such as calibration data. This can be especially helpful when a malfunction of the medical device, such as a pace maker or insulin pump, would cause a serious medical condition.

In some instances, a medical professional can also initiate regular checkups on their patients remotely, any time of the day, without scheduling an appointment, by initiating the request to communicate with the consumer medical device 140 through the mobile consumer device 110. This can help the medical professional work more efficiently.

In some embodiments, the request is initiated by a third party caregiver who would like to remotely check up on a dependent and/or the medical devices connected to the dependent through the Internet and/or another network connections.

Once the request has been made, the mobile consumer device 110 initiates communication with the consumer medical device 140 using a wireless communication such as Bluetooth, Wi-Fi, infrared or other wireless communication (220). Once the communication channel has been established, the user/medical professional/application is prompted to select the type of activity/procedure to perform and/or communication to initiate. The appropriately desired selection is then made to initiate the desired process.

In one embodiment, the selection and corresponding process is the collection of metric data from the consumer medical device (230). The mobile consumer device can collect historical and/or static data on the operation of the consumer medical device 140 as well as the biological condition or state of the user or patient wearing the medical device.

When collecting data from the consumer medical device 140, the mobile consumer device 110 provides data such as the settings of the consumer medical device, 140 a diagnostic report, and recent activity. By way of example, when used with a hearing aid, the report might include experienced frequency ranges and volumes of sounds experienced over a particular period of time, as well as volume settings and enabled filtering processes of the hearing aid. For an insulin pump, the reported data might include a flow rate or information about a dosage administered and blood glucose readings.

Another initiated process (act 240) can include providing update data to the consumer medical device. It will be appreciated, in this regard, that update data can include any data that is operable to alter a state or functionality of the medical device 140. One alteration is calibration. A hearing aid, for example must generally be calibrated at least once per year. This calibration entails adjusting the amplification of various frequency ranges; a task that currently requires a professional. Through several tests and adjustments communicated to the hearing aid via the mobile consumer device, a user can calibrate the hearing aid from home while avoiding an unnecessary appointment with a medical professional.

Another alteration is the enabling or disabling of certain functionalities of a consumer medical device. This can include, but is not limited to turning on or off enabled functionalities based on subscription settings and/or preferences of the user/medical professional. For instance, a hearing aid, prosthetic limb or other medical device may have certain features and sensory elements which the patient must pay to use.

An example of a functionality that the a user may wish to disable is the amplification of certain frequencies that cause annoying feedback in a malfunctioning hearing aid. In addition, the update could entail providing a software update. This update could be a regularly scheduled communication, or it could be initiated by the user to update and correct a malfunctioning consumer medical device 140.

The update data can also include instructions to initiate or to perform other processes at the medical device 140, such as the application of medicines, gathering of data, resetting of factory settings, altering factory settings, and so forth.

At any point in time, the mobile consumer device 110 can also participate in additional communications (250), which can include communications related to any of the foregoing processes or any other communication activities. This can include, for example, any follow-up communications for receiving additional updates or instructions and for performing additional analysis of the metric data for the one or more consumer medical devices 140. The additional communications can also include ancillary communications, such as video conferencing, teleconferencing or other communications that are facilitated by the mobile consumer device 110 and that relate specifically to the consumer medical device 140. In some embodiments, an interface is presented at the mobile consumer device 110 that reflects status information related to the consumer medical device 140 and that simultaneously provides communication information received from a third party system 160, such as the system of a medical professional, such that the interface simultaneously reflects data from the medical device 140 and the medical professional to the user at the mobile consumer device 110.

Another example of additional communication is the receipt and/or presentation of recommended user action. If metric data reports malfunction of a device, the recommended action could include sending the report to a medical professional, scheduling an appointment with a medical professional, immediately going to a hospital, or updating the device. If the recommended action is sending the report to a medical professional, depending on the settings of the mobile consumer device 110, the report will be manually or automatically sent from the mobile consumer device 101 to a pre-assigned medical professional whose contact information is stored in storage 124 of the mobile consumer device 110. If the recommended action is scheduling an appointment with a medical professional, the mobile consumer device 110 can contact the medical provider servers/systems 162 automatically or in response to user input, via the network connections 150 to either access the schedule of the medical professional to schedule an appointment for the user or to provide the phone number to call and schedule an appointment. Again, the information to perform these tasks is accessible through the storage 124 of the mobile consumer device 110.

If the recommended user action is immediately going to a hospital, the mobile consumer device can locate the nearest hospital and give directions or it can give the option to call an ambulance if the mobile consumer device is a mobile phone.

If the recommended action is to update the device, the mobile consumer device will recommend the type of update such as calibration, software update, enabling functionalities, or disabling functionalities.

One specific example, related to a hearing aid will now be provided. In this example, a smart phone is a mobile consumer device 110 that communicates with the hearing aid using Bluetooth capability of the smart phone and hearing aid. When the hearing aid malfunctions, it detects the malfunction and sends a signal to the smart phone requesting communication. The user is notified of the request via interfaces presented on the smart phone, including notifications generated by instant messaging, text messaging, voice messaging or medical application interfaces specific to the hearing aid.

The application interfaces can then initiate a particular process to update the hearing aid or to test the hearing aid, at the request of the user. Alternatively, the application interfaces can notify a medical professional of the condition for analysis and recommended actions.

In some instances, the user might have to provide authentication passwords to interact with the hearing aid (to perform testing and or to provide updates) and if he chooses to allow his audiologist to communicate with his hearing aid. The audiologist may also have to provide authentication prior to communicating with the hearing aid through the network connections 150 and smart phone link. The audiologist might request metric data for the settings of the hearing aid (if they are not already provided) to diagnose progressive hearing loss based on the adjustments that the user has made to the settings over time. The audiologist could also assist the user in calibrating the amplification of frequency ranges using the same method. In some instances, the calibrations can be performed automatically. In other instances, the user is instructed how to make manual adjustments. Either way, this can significantly increase the convenience and efficiency of the procedure by allowing the user/medical device to receive the requisite medical attention, while minimizing travel time and costs associated with performing the procedure.

In another example, related to the hearing aid, a user of the hearing aid can access an interface on their tablet, cell phone or smart device to turn up the sensitivity/volume on their hearing aid while watching television and to turn down the sensitivity/volume when reading a book or attending a loud concert. Another possible update could include streaming/playing music received as update data from the smart phone through the speakers of the hearing aid.

Accordingly, the embodiments disclosed herein provide methods, systems and computer program products for communicating between a mobile consumer device and a consumer medical device. Some exemplary forms of communication may include a Bluetooth communication channel connecting a smart phone with a hearing aid, but the scope of the embodiments disclosed herein extend to many forms of communication between a mobile consumer device and consumer medical devices such a Bluetooth, infrared, or Wi-Fi wireless communication channel connecting a mobile phone, tablet, or portable gaming device to one or more consumer medical devices such as hearing aids, prosthetics, insulin pumps, dialysis machines, pacemakers and other devices for the purpose of collecting metric data from or updating the consumer medical devices.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. A computer-implemented method for using a mobile consumer device to communicate with a hearing aid device, the method comprising:
   an act of a mobile consumer device associated with a patient, and which includes one or more processors, receiving a communication request from the hearing aid device of the patient to communicate with the hearing aid device that is connected to the patient, the communication request having been automatically generated by the hearing aid device in response to the hearing aid device detecting a predetermined condition corresponding to metric data that is associated with the hearing aid device;
   in response to the communication request, an act of the mobile consumer device identifying the hearing aid device and a communication channel to use in a communication between the hearing aid device and the mobile consumer device;
   an act of the mobile consumer device communicating with the hearing aid device via the communication channel;
   during the communication, generating a notification to the patient that is rendered at the mobile consumer device and that is operable to prompt the patient to update the hearing aid device; and
   after the patient's identity being authenticated, the mobile consumer device transmitting update data to the hearing aid device that is operable to update the hearing aid device.

2. The method recited in claim 1, wherein the predetermined condition detected by the hearing aid device is a malfunction of the hearing aid device.

3. The method recited in claim 1, wherein the predetermined condition is a low battery or low power condition.

4. The method recited in claim 1, wherein the update comprises at least one of: calibrating the hearing aid device, enabling new functionality of the hearing aid device, disabling at least one functionality of the hearing aid device, or updating the software of the hearing aid device.

5. The method recited in claim 1, wherein the method includes obtaining the metric data from the hearing aid device, the metric data corresponding to at least one of: functionality of the hearing aid device, historical settings of the hearing aid device, static settings of the hearing aid device, or data corresponding to a biological condition of the patient.

6. The method of claim 1, wherein the method includes both providing an update for the hearing aid device and obtaining the metric data from the hearing aid device.

7. The method recited in claim 1, wherein the method includes providing the update during the communication, and wherein the update comprises a volume control instruction that is operable to adjust a volume setting of the hearing aid device when received by and processed by the hearing aid device.

8. The method recited in claim 1, wherein the method includes providing the update during the communication, and wherein the update comprises a filter control instruction setting that is operable to adjust a filter setting of the hearing aid device.

9. The method recited in claim 1, wherein the mobile consumer device comprises one or more of a tablet computer.

10. The method recited in claim 1, wherein the communication channel is a Bluetooth wireless communication channel.

11. The method recited in claim 1, further comprising automatically initializing insurance processing by routing information about the predetermined condition and/or the update data to one or more insurance companies.

12. The method recited in claim 1, further comprising enabling and/or disabling one or more functionalities of the hearing aid device according to the patient's subscription level.

13. One or more recordable-type computer hardware storage device having stored thereon computer executable instructions that, when executed by one or more processors of a mobile consumer device, implement a method for communicating with a hearing aid, the method comprising:
   receiving a communication request from a hearing aid device of a patient to communicate with the hearing aid device, the communication request having been automatically generated by the hearing aid device in response to the hearing aid device detecting a predetermined condition corresponding to metric data that is associated with the hearing aid device;
   in response to the communication request, an act of identifying the hearing aid and a communication channel to use in a communication with the hearing aid;
   communicating with the hearing aid via the communication channel;
   during the communication, generating a notification to the patient that is rendered at the mobile consumer device and that is operable to prompt the patient to update the hearing aid device; and
   after the patient's identity being authenticated, the mobile consumer device transmitting update data to the hearing aid device that is operable to update the hearing aid device.

14. The one or more computer storage device of claim 13, wherein the one or more computer storage media comprises the hearing aid and wherein the computer executable instructions are downloadable from the hearing aid to the mobile consumer device.

15. A computing system comprising:
at least one processor;
recordable-type storage media having stored instructions which, when executed by the at least one processor, implement a method for using a mobile consumer device to communicate with a hearing aid device, the method comprising:
   an act of the mobile consumer device associated with a patient, and which includes one or more processors, receiving a communication request from the hearing aid device of the patient to communicate with the hearing aid device that is connected to the patient, the communication request having been automatically generated by the hearing aid device in response to the hearing aid device detecting a predetermined condition corresponding to metric data that is associated with the hearing aid device;
   in response to the communication request, an act of the mobile consumer device identifying the hearing aid device and a communication channel to use in a communication between the hearing aid device and the mobile consumer device;
   an act of the mobile consumer device communicating with the hearing aid device via the communication channel;
   during the communication, generating a notification to the patient that is rendered at the mobile consumer device and that is operable to prompt the patient to update the hearing aid device; and
   after the patient's identity being authenticated, the mobile consumer device transmitting update data to the hearing aid device that is operable to update the hearing aid device.

16. The system recited in claim 15, wherein the method further comprises adjusting a volume of the hearing aid device in response to user input received at the mobile consumer device.

* * * * *